United States Patent [19]

Repper et al.

[11] Patent Number: 5,543,137
[45] Date of Patent: Aug. 6, 1996

[54] METHOD OF PROTECTING AGAINST SUNBURN

[76] Inventors: George R. Repper; Helen Z. Repper, both of 2903 Dadmun Ct., Fairfax, Va. 22031

[21] Appl. No.: 334,229

[22] Filed: Nov. 4, 1994

Related U.S. Application Data

[63] Continuation-in-part of Ser. No. 308,444, Sep. 19, 1994.
[51] Int. Cl.$^6$ .............................. A61K 7/40; A61K 7/42
[52] U.S. Cl. .............................. 424/59; 424/9.1; 424/60; 424/63
[58] Field of Search .................. 424/59, 60, 63, 424/7.1, 9.1

[56] References Cited

U.S. PATENT DOCUMENTS

| | | | |
|---|---|---|---|
| 3,988,437 | 10/1976 | Bradner | 424/59 |
| 4,256,664 | 3/1981 | Epstein et al. | 424/59 X |
| 4,818,491 | 4/1989 | Fariss | 422/56 |
| 5,028,792 | 7/1991 | Mullis | 250/474 |
| 5,045,317 | 9/1991 | Chess et al. | 424/401 |
| 5,331,140 | 7/1994 | Stephany | 235/462 |

*Primary Examiner*—Shelley A. Dodson
*Attorney, Agent, or Firm*—Rothwell, Figg, Ernst & Kurz

[57] ABSTRACT

A method and kit for protecting a body against sunburn utilize application of a chemical sunscreen composition to external portions of a body, with the sunscreen composition being capable of fluorescing at a first visible wavelength under illumination from light of a second wavelength. The body is illuminated with light of the second wavelength so as to cause the sunscreen to fluoresce. The body is viewed while the body is under illumination of the second wavelength, so as to identify any non-fluorescing, missed external portions of the body to which the sunscreen was not previously applied. The sunscreen is further applied to any missed body portions.

20 Claims, 1 Drawing Sheet

METHOD OF PROTECTING AGAINST SUNBURN

This application is a continuation-in-part of copending U.S. application Ser. No. 08/308,444 filed Sep. 29, 1994.

BACKGROUND OF THE INVENTION

1. Field of the Invention

The present invention relates to a method of protecting against sunburn.

2. Description of the Background Art

Exposure to direct sunlight is known to be harmful to human skin. In the short term, there is a risk of severe and painful sunburn. Additionally, exposure to direct sunlight increases the risk of skin cancer, and can cause visible degradation of skin appearance over time.

Despite knowledge of the harmful effects of direct sunlight on human skin, many people continue to subject their skin to such exposure, for example, during outdoor sports such as swimming, boating, tennis, golf and the like.

In societies where tanned bodies are fashionable, some persons intentionally sunbathe to expose their skin to the sun's radiation, thereby promoting cosmetic tanning of the skin.

Chemical sunscreen products are known in the art which, when applied to the skin, reduce the risk of sunburn, skin cancer and visible degradation of skin appearance. However, when such chemical sunscreen products are used, no protection is provided to those missed areas of the skin to which the sunscreen inadvertently is not applied. Furthermore, protection is lost to skin areas from which sunscreen has been washed off by water, diluted or carried off by perspiration, or rubbed off by some other means. Under such circumstances, severe and painful sunburn can repeatedly result, despite conscientious use of sunscreen. Such repeated sunburn accelerates degradation of skin appearance, and substantially increases the risk of skin cancer and death.

In view of the above, it is quite apparent that there remains a critical need in the art for new and improved methods of protecting against sunburn.

SUMMARY OF THE INVENTION

In accordance with the present invention, a method of protecting a body against sunburn comprises providing a chemical sunscreen composition which fluoresces at a visible first wavelength upon being illuminated with light of a second wavelength different from the first wavelength. The chemical sunscreen composition is applied to the body, and the body is illuminated with light of the second wavelength so as to cause sunscreen applied to the body to fluoresce at the first wavelength. The body is viewed while the body is under illumination of the light of the second wavelength, so as to identify any non-fluorescing missed external body portions to which the sunscreen was not applied. The sunscreen is then further applied to the missed body portions.

The invention is further applicable to a kit for carrying out the invention.

DETAILED DESCRIPTION OF THE PREFERRED EMBODIMENTS

As indicated above, one aspect of the invention is a method of protecting a body against sunburn. This method involves application of a sunscreen composition to external portions of a body, such as bare, uncovered or unclothed human skin at risk of exposure to direct sunlight. Sunscreen compositions typically disappear, i.e., are invisible after application to the skin, thereby making it difficult or impossible to determine where the sunscreen has been applied, or if a sufficient amount has been applied for protection.

Sunscreen compositions which are suitable for use in accordance one aspect of the present invention are capable of fluorescing under black light illumination.

The term "black light" is well understood in the art to mean ultraviolet lamps of the type which commonly are sold in novelty stores and the like, such as a Minerallight Ultraviolet Lamp, Short Wave S1 2537 manufactured by Ultraviolet Products, Inc., San Gabriel, Calif., U.S.A.

However, the present invention is not limited to utilization of sunscreens which fluoresce under black light illumination. The invention is directed to utilization of chemical sunscreen compositions which fluoresce at any visible first wavelength upon being illuminated with light of any second wavelength different from the first wavelength. The source of the second wavelength can be a black light or any suitable source, including sunlight, or artificial sources of light such as incandescent, fluorescent or halogen lights, etc.

Light of the fluorescing first wavelength is within the range of about 4000–7000 Å, whereas light of the illuminating second wavelength generally is greater than about 2000 Å and less than about 4200 Å. In preferred embodiments, the second wavelength is less than about 4000 Å, and/or greater than about 2500 Å.

In other embodiments, the illuminating second wavelength is about 3500 Å or lower, and/or about 2800 Å or higher. In further embodiments, the second wavelength is about 2800 Å or higher, but less than about 4000 Å, and more preferably about 3200 Å or lower. In still other embodiments, the second wavelength is about 3000 Å or higher, but less than about 4000 Å. Preferably, the second wavelength is between about 2000–4000 Å, more preferably 2500–3500 Å and most preferably 2800–3200 Å.

Suitable sunscreens are taught, for example, in U.S. Pat. No. 4,256,664, and the like.

For example, suitable sunscreens may fluoresce strongly at about 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, or 7000 Angstroms (Å), or any intervening wavelength.

In accordance with one aspect of the invention, at least one optical filter means is provided, for substantially filtering visible spectrum light except for light of substantially the first wavelength, the filter means permitting light of the first wavelength substantially to pass therethrough.

Figure 2:
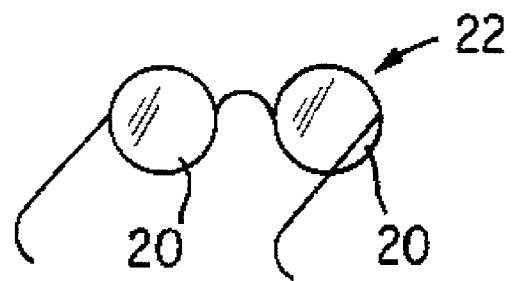
FIG. 2 is a perspective view of eyeglass filters in accordance with one embodiment of the present invention.

In preferred embodiments, the optical filter means is provided as lenses 20 in a pair of eyeglasses 22, as shown in FIG. 2.

Advantageously, the filter has an optical bandpass narrower than about 500 Å, within which bandwidth the first wavelength is present. The filter bandpass preferably is narrower than about 300 Å, more preferably narrower than about 200 Å, and most preferably about 100 Å or narrower, e.g., about 50 Å. For example, a sunscreen which fluoresces strongly at about 4500 Å can utilize a filter having a bandpass of between 4250–4750 Å or narrower, preferably between about 4350–4650 Å or narrower, more preferably between about 4400–4600 Å or narrower, and most preferably between about 4450–4550 Å or narrower, e.g., 4475–4525 Å.

According to this embodiment, a body to which sunscreen in accordance with the present invention has been applied is illuminated with light of the second wavelength so as to cause the sunscreen to fluoresce at the first wavelength.

The body is viewed under illumination from the light of the second wavelength so as to identify any missed external portions of the body to which the sunscreen was not previously applied, whereupon sunscreen is further applied to the missed body portions.

The above steps can be repeated until all exposed external body portions fluoresce under illumination of the second wavelength, indicating that the exposed body portions are coated with sunscreen. Thus, the body can be further illuminated with the light of the second wavelength, and further viewed so as to identify any further missed body parts to which sunscreen was not applied. Sunscreen then can be applied to any additional missed body portions.

Additionally, sunscreen can be reapplied to any areas which do not fluoresce strongly, indicating a thin layer or coating of sunscreen. According to this embodiment, the sunscreen is reapplied to body portions to provide a substantially uniform fluorescence of exposed body portions under illumination of the second wavelength.

Advantageously, sunscreen in accordance with the present invention is further applied while viewing the body under a black light and/or through the optical filter means under illumination of the second wavelength from any suitable source, so as to coat any missed external body portions of the body and/or provide a substantially uniform fluorescence of exposed body portions.

In preferred embodiments, prior to application of sunscreen, the body is illuminated by light of the second wavelength, and sunscreen in accordance with the present invention is applied to exposed external portions of the body while viewing the body under a black light and/or through the filter means under illumination with light of the second wavelength from any suitable source.

After applying sunscreen to the body in accordance with the present invention, the body can be subjected to an activity selected from the group consisting of, for example, contacting the body with liquid (e.g., water), exposing the body to sunlight, subjecting the body to physical activity, and combinations thereof. Thereafter, the body can again be viewed under a black light and/or through the filter means under illumination of light of the second wavelength from any suitable source, and sunscreen applied to any external body portions missing sunscreen or not fluorescing strongly.

The invention also is applicable to a kit which includes a chemical sunscreen composition as defined above, and further including an optical filter means as defined above and/or a black light lamp. In preferred embodiments, the kit further includes instructions for applying the sunscreen to external portions of a body, viewing application of the sunscreen under a black light lamp and/or through the filter means under illumination with suitable light, and further applying the sunscreen to any missed body portions to which the sunscreen had not been applied, or body portions not fluorescing strongly.

Figure 1:
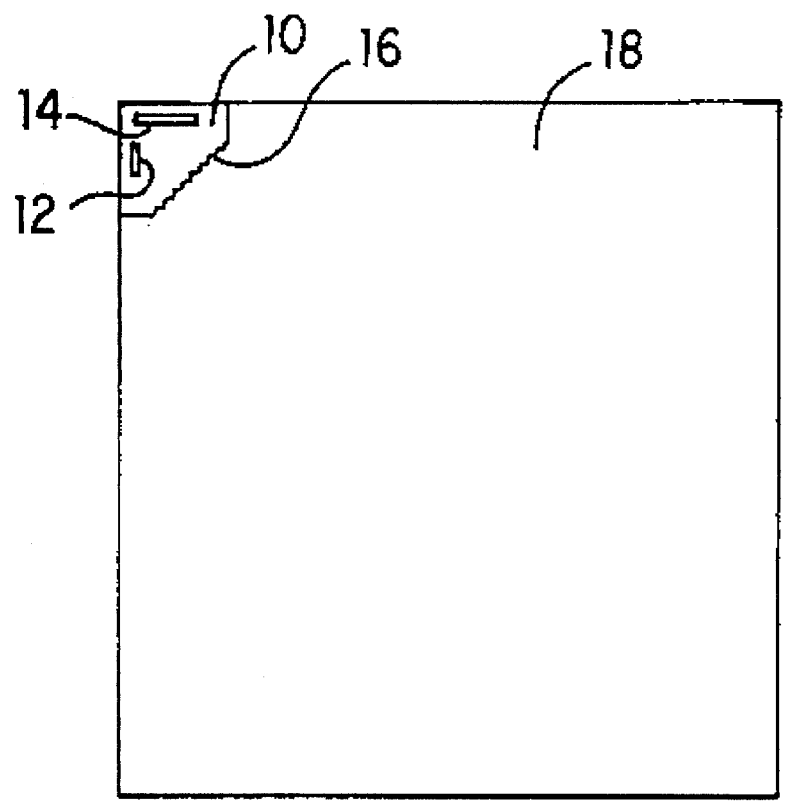
FIG. 1 an elevational view, schematically illustrating a sunscreen viewing booth in accordance with one aspect of the invention, and an installation thereof.

One embodiment of the present invention is a sunscreen viewing booth 10, schematically shown in FIG. 1. The sunscreen viewing booth includes a black light lamp 12 for causing black light-fluorescing sunscreen to fluoresce.

A mirror 14 is provided, for viewing a body under illumination of black light 12, so as to view application of fluorescing sunscreen to the body.

External light, such as sunlight or light from normal incandescent or fluorescent lamps, may prevent viewing of fluorescing sunscreen during illumination with the black light. Accordingly, means such as curtain 16 are provided for reducing illumination of the body by external light, so that fluorescence of said sunscreen on said body can be viewed.

In accordance with one embodiment, a sunscreen viewing booth according to the invention includes instructions for applying sunscreen to external portions of the body, viewing application of the sunscreen under illumination from the black light lamp, and further applying the sunscreen to any missed body portions to which the sunscreen had not previously been applied, or to weakly fluorescing areas of the body.

In preferred embodiments, a sunscreen viewing booth according to the present invention is positioned in or adjacent an area 18 at or near a location where exposure to the sun may take place. Thus, area 18 can be a hotel, beach, swimming pool or other body of water, or any outdoor area for participation in sunbathing or sports such as tennis, golf, swimming, boating, etc. Thus, the invention encompasses a sunscreen viewing booth as described above, positioned in or adjacent a hotel, on or adjacent a beach, adjacent a swimming pool or other body of water, or adjacent any outdoor area where sunbathing or participation in sports such as tennis, golf, swimming, boating, etc., can take place.

From the above, it is readily apparent that the present invention solves the problem of not knowing where on the body sunscreen has been applied, where it has been thinly applied or where it has been missed altogether.

The present invention also solves the problem of determining if sunscreen has been washed or rubbed off, or removed by some other means.

The present invention thus solves a long felt and critical need in the art for a method of preventing sunburn, which heretofore has not been fully met by any known methods or products.

Use of the present invention can prevent countless cases of painful sunburn, thereby avoiding the misery resulting therefrom.

Use of the invention can also reduce the risk of skin cancer and premature death resulting therefrom, and avoid visible degradation of skin appearance over time, due to exposure to damaging rays of sunlight.

We claim:

1. A method of protecting a body against sunburn, comprising:
   (a) providing a chemical sunscreen composition which fluoresces at a visible first wavelength upon being illuminated with light of a second wavelength different from said first wavelength;
   (b) applying said chemical sunscreen composition to external portions of a body;
   (c) illuminating the body with light of said second wavelength so as to cause said sunscreen to fluoresce at said first wavelength;

(d) viewing the body while said body is under illumination of said light of said second wavelength so as to identify any non-fluorescing, missed external body portions of said body, to which said sunscreen was not applied in steps (b); and (e) further applying said sunscreen to the missed body portions.

2. The method of claim 1, further including the step of providing at least one optical filter means for substantially filtering visible spectrum light except for light of substantially said first wavelength, said filter means permitting light of said first wavelength substantially to pass therethrough; wherein, in step (d), said viewing of said body is through said filter means.

3. The method of claim 2, wherein said sunscreen is further applied in steps (e) while viewing said body through said filter means under illumination from said light of said second wavelength.

4. The method of claim 2 wherein, after steps (e), the body is further illuminated with said light of said second wavelength, and further viewed through said filter means under illumination of said second wavelength, so as to identify any further missed body portions to which sunscreen was not applied, and then further applying said sunscreen to the further missed body portions.

5. The method of claim 2, wherein steps (c) through (e) are repeated so as to provide a substantially uniform coating of said sunscreen on external portions of said body.

6. The method of claim 2, wherein said sunscreen is applied so as to provide a substantially uniform fluorescence of exposed body portions under illumination of said second wavelength.

7. The method of claim 2 wherein, prior to step (b), the body is illuminated by said second wavelength and steps (b) is carried out while viewing the body through said filter means under illumination of said second wavelength.

8. The method of claim 2 wherein, after step (e), the body is subjected to an activity selected from the group consisting of contacting the body with liquid, exposing the body to sunlight, subjecting the body to physical activity, and combinations thereof, and thereafter, the body is again viewed through said filter means under illumination of said second wavelength, and sunscreen is applied to any external body portions missing sunscreen.

9. The method of claim 2, wherein said first wavelength is in the range of about 4000–7000 Å, and said second wavelength is greater than about 2000 Å and less than about 4200 Å.

10. The method of claim 9, wherein said second wavelength is between about 2000–4000 Å.

11. The method of claim 10, wherein said second wavelength is between about 2500–3500 Å.

12. The method of claim 11, wherein said second wavelength is between about 2800–3200 Å.

13. The method of claim 9, wherein said filter has an optical bandpass of less than about 300 Å.

14. The method of claim 9, wherein said filter has an optical bandpass of less than about 100 Å.

15. A kit comprising:

(a) a chemical sunscreen composition as defined in claim 1, which fluoresces at a visible first wavelength upon being illuminated with light of a second wavelength different from said first wavelength; and (b) optical filter means as defined in claim 2, for substantially filtering visible spectrum light except for light of substantially said first wavelength, said filter means permitting light of said first wavelength substantially to pass therethrough.

16. The kit of claim 15, further including instructions for applying said sunscreen to external portions of a body, viewing application of the sunscreen through said filter means under illumination of light including said second wavelength, and further applying said sunscreen to any missed body portions to which said sunscreen had not previously been applied.

17. The kit of claim 15, wherein said optical filter means is present in a pair of eyeglasses.

18. The kit of claim 15, wherein said first wavelength is in the range of about 4000–7000 Å, and said second wavelength is greater than about 2000 Å and less than about 4200 Å.

19. The kit of claim 18, wherein said filter has an optical bandpass of less than about 300 Å.

20. A method of applying a chemical composition to external portions of a body, comprising:

(a) providing a chemical composition which fluoresces at a visible first wavelength upon being illuminated with light of a second wavelength different from said first wavelength;

(b) applying said chemical composition to external portions of a body;

(c) illuminating the body with light of said second wavelength so as to cause said composition to fluoresce at said first wavelength;

(d) viewing the body while said body is under illumination of said light of said second wavelength so as to identify any non-fluorescing, missed external body portions of said body, to which said composition was not applied in step (b); and (e) further applying said composition to the missed body portions.

* * * * *